United States Patent [19]

Hennicke et al.

[11] 4,246,086
[45] Jan. 20, 1981

[54] METHOD AND APPARATUS FOR COATING DENTAL CROWNS AND BRIDGES

[75] Inventors: Hans W. Hennicke, Clausthal-Zellerfeld; Joachim Weiss, Bremen-Oberneuland, both of Fed. Rep. of Germany

[73] Assignee: Bego Bremer Goldschlagerei Wilh. Herbst, Bremen, Fed. Rep. of Germany

[21] Appl. No.: 877,525

[22] Filed: Feb. 13, 1978

[30] Foreign Application Priority Data

Feb. 11, 1977 [DE] Fed. Rep. of Germany ....... 2705770

[51] Int. Cl.³ .................. C25D 1/14; C25D 13/02; C25D 17/02
[52] U.S. Cl. .................. 204/181 N; 204/181 F; 204/181 T; 433/202
[58] Field of Search ........... 204/181 F, 181 R, 181 T, 204/181 N; 433/202

[56] References Cited

U.S. PATENT DOCUMENTS

| | | | |
|---|---|---|---|
| 4,085,021 | 4/1978 | van der Vliet | 204/181 N |
| 4,125,442 | 11/1978 | Rogers | 433/202 |

Primary Examiner—Howard S. Williams
Attorney, Agent, or Firm—Sughrue, Rothwell, Mion, Zinn and Macpeak

[57] ABSTRACT

A controlled layer of base mass is uniformly applied to a dental crown or bridge 10 of noble metal alloy by electrophoretic separation in a glass container 14 after an intermediate layer of galvanized zinc or tin is first applied in a container 13. The intermediate layer may be omitted if the crown or bridge is made of a non-noble metal alloy. The containers are provided with semi-cylindrical cathodes 15, 16 coupled to an electrical supply by jack plugs 19, 20. The crown or bridge serves as the anode and is held by tongs 21, 22 connected by cables 23, 24 to the power supply, and both the magnitudes and durations of the bath currents are adjustable. The liquid suspension of the base mass in the electrophoretic bath is maintained by a magnetic stirrer 27.

20 Claims, 3 Drawing Figures ns and Bridges

BACKGROUND OF THE INVENTION

This invention relates to a method and apparatus for producing dental crowns and bridges by the electrophoretic application of a layer of base mass on a rust-proof base article, such as a noble metal nickel alloy.

Dental crowns and bridges customarily comprise a metallic base blank of a noble or non-noble metal alloy, on which layers or strata of dentin and cutting mass are applied in the visible surface areas of the teeth to outwardly create the appearance of natural teeth.

The application of the non-metallic layers onto the base blank has hitherto been an expensive manual process in dental engineering. The base blank is first washed in acetic acid ethyl ester and then rinsed with distilled water. A first layer of base mass is then applied manually with a brush, and solidified by firing in a vacuum furnace, after which a second layer of base mass is brushed on and fired. Next a layer of dentin and cutting mass is applied with a brush onto the layers of base mass and fired in the vacuum furnace, after which at least one additional dentin or cutting mass layer is so applied. After solidification the workpiece is shaped by surface grinding or the like, color-masses are brushed on at certain places, and a final polish firing takes place.

The superposed layers of dentin and cutting mass are anchored onto the metallic base blank via the base mass layers. It is essential that the base mass be applied to form a very thin and uniform layer, which requires considerable manual effort and skill.

SUMMARY OF THE INVENTION

The present invention improves the production of dental crowns, bridges, etc. by providing a much simpler, easier and quicker way to apply the base mass layer(s). The process according to the invention is characterized by the application of the base mass layer to the base blank by electrophoretic separation. The layers of base mass produced in this manner have a homogeneous structure, a dense texture and a uniform layer thickness. The electrophoretic process also enables the accurate determination of the desired layer thickness, within a range of 80 to 100 $\mu$m.

The electrophoretic separation effect for the production of coatings on large iron workpieces is known in the enamelling arts. Electrophoretic enamelling uses an immersion process in which the enamel is applied with a DC current. The workpiece constitutes the positive electrode, and the negative electrodes are disposed in an aqueous suspension of an enamel frit.

This invention is based on the realization that electrophoresis is surprisingly suitable for the coating of dental engineering workpieces made of non-ferrous metals, namely noble metal alloys or non-noble metal alloys, with a layer of base mass. The base blank is submerged in an electrophoresis bath in which the base mass is suspended. With base blanks made of noble metal alloys, a metallic intermediate layer of galvanized zinc or tin is applied prior to the application of the base mass layer by electrophoresis.

The apparatus according to the invention is preferably equipped with two insulatory containers of glass or the like disposed on a base. One of the containers accommodates a galvanic bath for the pretreatment of workpieces made of noble metal alloys, while the electrophoretic coating is carried out in the other container. Curved cathode plates are disposed in both containers, and are connected to a suitable current supply by electrical cables and plugs.

DETAILED DESCRIPTION OF THE PREFERRED EMBODIMENT

Figure 1:
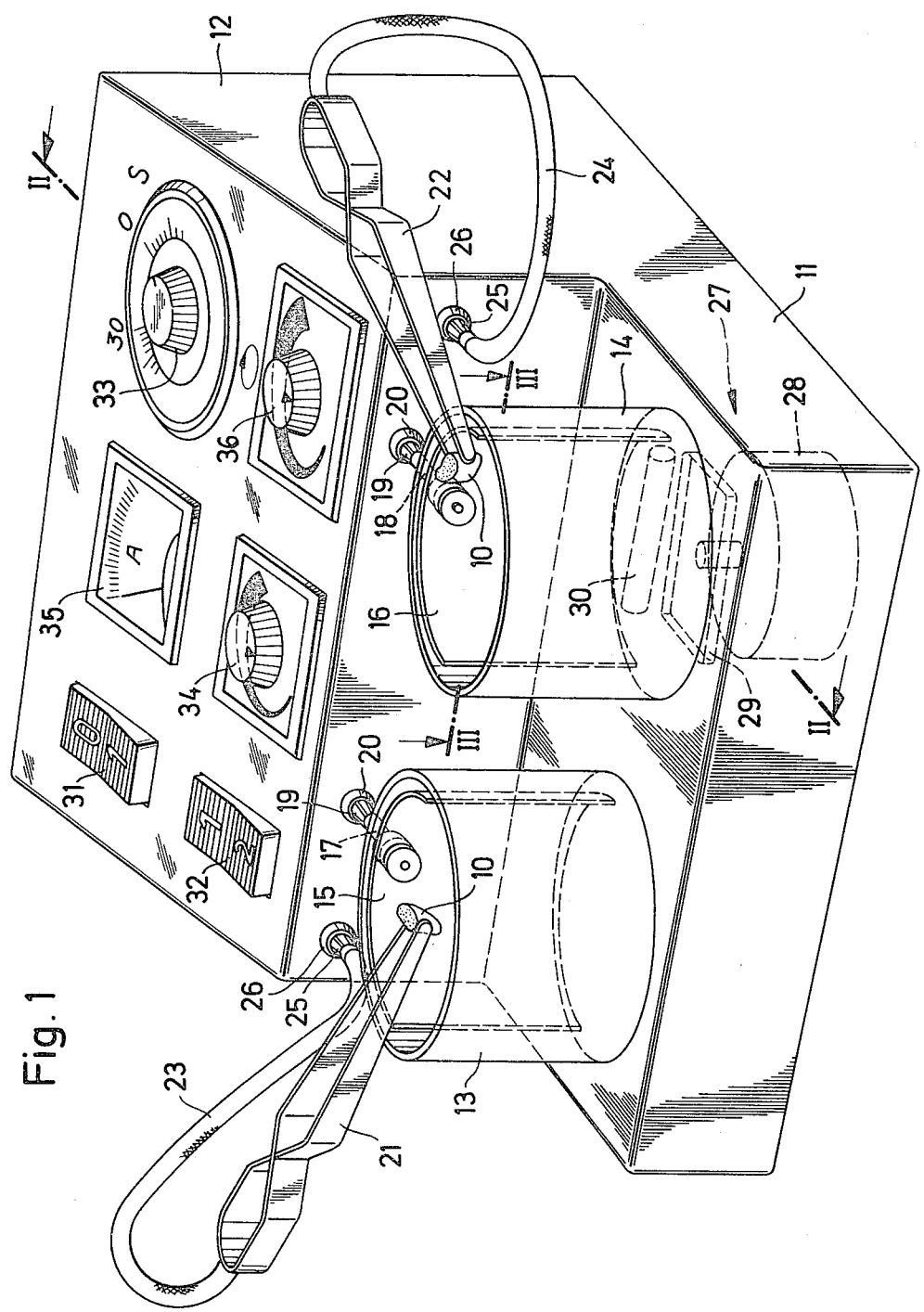
FIG. 1 shows a perspective view of an apparatus according to the invention.
Figure 2:
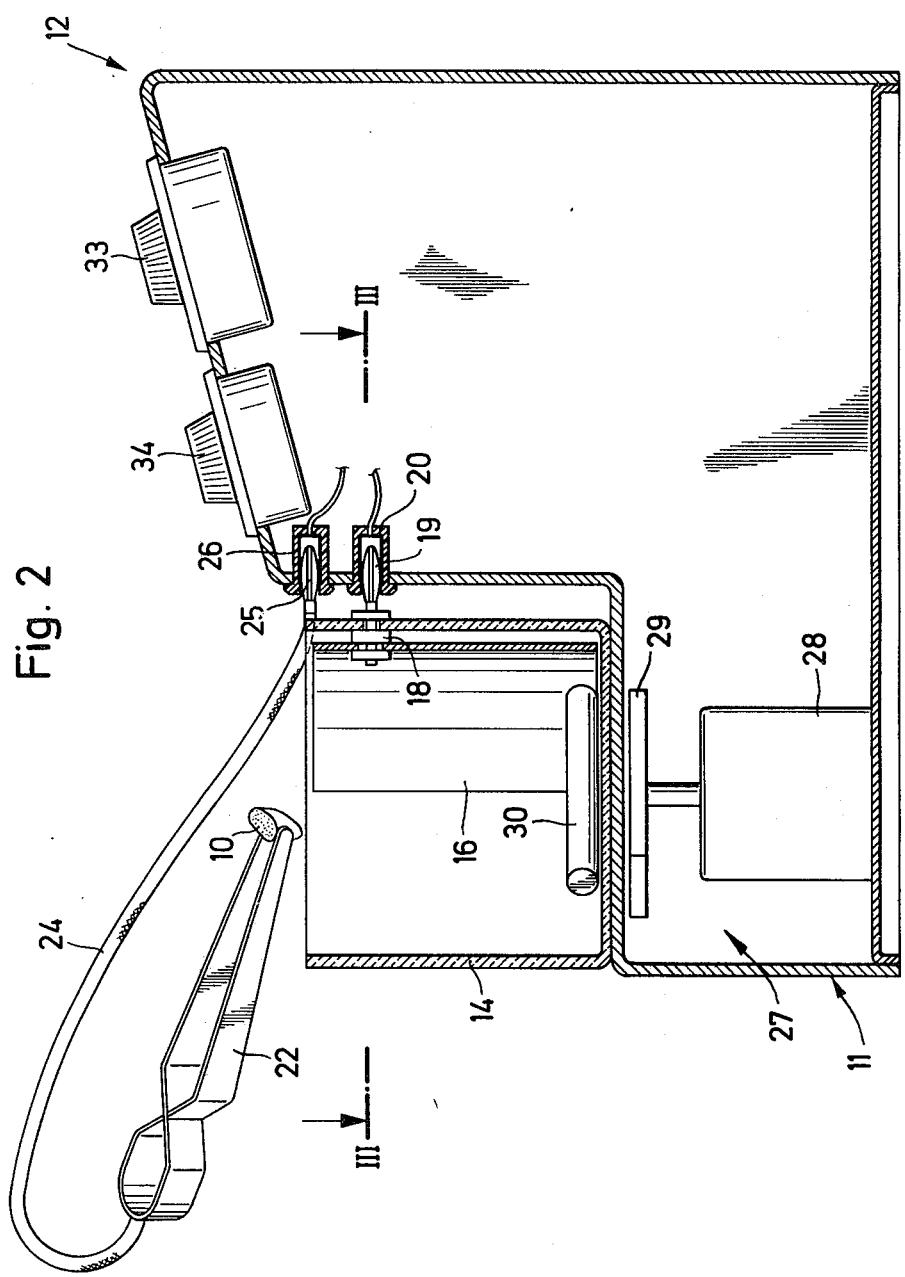
FIG. 2 shows a cross-sectional view of the apparatus according to FIG. 1.
Figure 3:
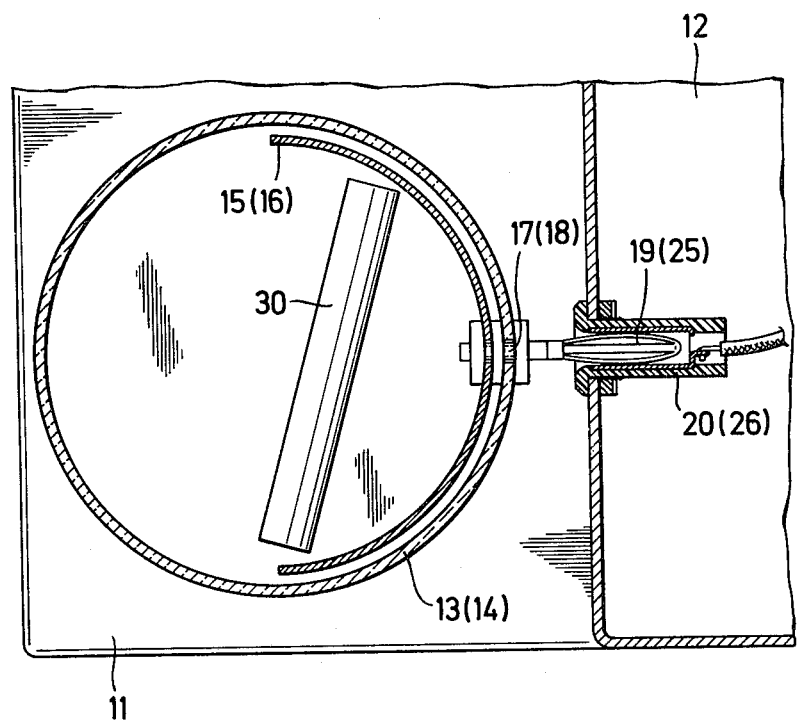
FIG. 3 shows a plan view of a container outline, in an enlarged scale.

The apparatus shown in the drawings is equally suitable for the treatment of dental engineering workpieces 10 made of noble metal alloys and for such workpieces made of non-noble metal alloys, for example, nickel alloys. These workpieces 10 may be individual crowns as shown in the drawing, or bridges developed in the form of an arch corresponding to the arrangement of teeth in a denture.

The apparatus includes a base 11 having an upstanding housing 12 to the rear. A container 13 for a galvanic bath and a container 14 for an electrophoretic bath are accommodated on the base 11. The containers 13 and 14 are made of an electrically non-conductive material, for example, glass.

Cathodes 15 and 16 are disposed in the containers 13 and 14, respectively. The cathode 15 may be a zinc jacket for the galvanization of the workpiece 10, while the cathode 16 in the container 14 may be stainless steel (V2A). In both cases, the cathodes have an arc-shaped outline concentric to the circular containers and extending over approximately half of the container circumference. The cathodes may also be shaped such that their curvatures correspond to the average curvature of a bridge workpiece whereby when such a workpiece is submerged in a container bath its side facing the cathode is approximately equidistant therefrom at all points. Releasable extension pieces may also be provided for the cathodes to enlarge them by widening their peripheral and/or bottom areas whereby coatings may be carried out on all sides.

The cathodes 15 and 16 may be coupled to a source of current via electrical connections 17 and 18 passing through the walls of the containers 13 and 14. These connections 17, 18 are insertable into corresponding sockets 20 in the housing 12 by split plug jacks 19. The workpiece 10 serves as an anode. Specifically, the metallic base blank of a crown, a bridge or the like is gripped by an electrically conductive holder such as tongs 21 or 22 and submerged into a container bath. The tongs are connected to the housing 12 via lines 23, 24, split plug jacks 25 and sockets 26. A stirring mechanism for the container 14 of the electrophoresis bath consists of a magnetic stirrer 27 including a motor 28 and a magnetic plate 29 housed in the base 11. A bar 30 in the container 14 is driven by the rotating magnetic plate 29 to provide a stirring or agitating effect in the electrophoresis bath.

The housing 12 contains the necessary equipment for the transformation and regulation of the input currents and also switching and control devices operable from the outside. These include an on-off switch 31, a switch 32 for alternately supplying current to one or the other of the containers 13, 14, and a timer clock 33 for controlling the duration of the current supply. A rheostat 34 controls the current magnitude, as read on ammeter 35, and a rheostat 36 controls the drive speed of the magnetic stirrer 27.

For the production of a crown with a base blank made of noble metal alloy, the base blank workpiece 10 is first submerged in an acid activating bath (not shown) preferably consisting of a 3% HCl solution with 3 g of copper sulfate ($CuSO_4$) and 1 liter of water. After such activation the workpiece 10 is rinsed with distilled water.

The activated workpiece 10 is then gripped by the tongs 21 and submerged in the galvanic bath in the container 13, where an intermediate zinc layer is applied galvanically to a maximum thickness of 1 $\mu$m. The zinc plating bath may have a known composition. The intermediate layered workpiece 10 is then again rinsed with distilled water.

The workpiece 10 is next gripped by the tongs 22 and submerged in the electrophoretic bath in the container 14. This bath consists of a customary dental base mass suspended in distilled water, such suspension being maintained by appropriately adjusting the speed of the magnetic stirrer 27. The commercially obtainable dental base mass sold under the trade designation "Opaker No. 13" by Ivoclar has proven particularly favorable for the electrophoretic coating, without the addition of zirconium dioxide/baddeleyite mineral. The base mass, which has a large proportion of an electrodepositable material such as tin dioxide, should have a very fine and uniform grain. The electrophoretic bath may be composed of a mixture of 100 g of base mass, 50 ml of methyl cellulose adjusting agent and 50 ml of distilled water.

The electrophoretic coating is applied in a matter of seconds using a voltage range of 5 to 40 V, depending on the compositions of the base mass and the bath. The thickness of the layer is determined by the adjustable duration of the current supply, whose intensity is adjusted automatically depending on the size or surface area of the workpiece 10. The duration of the current supply is set by the timer clock 33.

The workpiece 10 is again rinsed with distilled water after completion of the base mass coating process, and is then processed further in the customary manner by firing in a vacuum furnace. The dentin and cutting mass may be applied directly on the base mass layer produced by electrophoresis. Thus, a renewed coating with base mass is not required.

With base blanks made of non-noble metal alloys such as nickel alloy, the intermediate layer of zinc or tin plating may be omitted. Such workpieces may thus be submerged into the electrophoresis bath container 14 immediately after the above described activation and rinsing in distilled water. The electrophoretic coating is then accomplished in the same manner as with workpieces made of noble metal alloys.

The electrophoresis layers provided according to the invention are not only of exceptionally high quality, but they also lead to better adhesion of the ceramic layers on metal.

What is claimed is:

1. A process for producing metal-ceramic dental crowns and bridges by applying layers on a base blank comprising the steps of:

(a) applying an opaque layer of base mass to a base blank consisting of a precious metal or nickel alloy by electrophoretic precipitation, and
    (b) subsequently applying a dentine layer and an outer lustrous layer to the opaque layer of base mass.

2. Process as in claim 1, wherein the base blank is a noble metal alloy and is first provided with an intermediate metallic layer of zinc or tin before the base mass layer is applied by electrophoretic coating.

3. Process as in claim 2, wherein the intermediate metallic layer is applied to the base blank by galvanic separation.

4. Process as in claim 3, wherein the base blank is submerged in an acid activating bath prior to the application of the intermediate metallic layer.

5. Process as in claim 4, wherein the base mass comprises a large proportion of tin dioxide without zirconium dioxide.

6. Process as in claim 5, wherein the base blank is submerged in an electrophoretic coating bath in which the base mass is suspended.

7. Process as in claim 6, wherein the electrophoretic bath comprises distilled water in which the base mass is suspended by an adjusting agent, such as methyl cellulose.

8. Process as in claim 6, wherein the electrophoresis bath is continuously stirred to prevent the settling of the suspended base mass.

9. Process as in claim 6, wherein the electrophoresis bath comprises a mixture in the ratio of 100 g base mass, 50 ml adjusting agent, and 50 ml of distilled water.

10. Process as in claim 1, wherein the operating voltage for the electrophoretic coating of the base blank is between 5 V and 40 V.

11. An apparatus for carrying out the process defined in claims 1 to 10, characterized by at least one container (14) formed of electrically non-conductive material, such as glass or plastic, and a cathode (16) disposed in the container, preferably formed of stainless steel (V2A).

12. Apparatus as in claim 11, wherein the cathode has a semi-cylindrical configuration and is concentrically disposed on the inside of the container.

13. Apparatus as in claim 12, wherein the shape of the cathode generally conforms to the shape of the base blank (10) to provide a more uniform spacing between the base blank and the cathode surfaces.

14. Apparatus as in claim 11, wherein the cathode is provided with releasable enlargement tongues on its bottom and sides.

15. Apparatus as in claim 11, wherein the cathode is releasably coupled to a current supply by a connector (18) penetrating the wall of the container and a jack plug connector.

16. Apparatus as in claim 11, comprising a base (11) for supporting the container and a housing (12) therebehind for accommodating electrical control and regulating means.

17. Apparatus as in claim 16, further comprising a magnetic stirring mechanism for the container (14) mounted in the base (11).

18. Apparatus as in claim 17, further comprising at least one additional container (13) for a galvanic bath disposed beside the container (14) on the base (11).

19. Apparatus as in claim 18, wherein the galvanic bath container is provided with a semi-cylindrical cathode (15) of zinc or tin.

20. Apparatus as in claim 19, further comprising tongs (21, 22) for gripping the base blank (10) connected to electrical power supply lines (23, 24).

* * * * *